United States Patent [19]

Hada

[11] Patent Number: 5,212,717
[45] Date of Patent: May 18, 1993

[54] COMPUTED TOMOGRAPHY SCANNER APPARATUS

[75] Inventor: Tetsurou Hada, Tochigi, Japan

[73] Assignee: Kabushiki Kaisha Toshiba, Kawasaki, Japan

[21] Appl. No.: 721,311

[22] Filed: Jun. 26, 1991

[30] Foreign Application Priority Data

Jun. 27, 1990 [JP] Japan .................................. 2-169382

[51] Int. Cl.⁵ .............................................. G21K 1/04
[52] U.S. Cl. ............................................ 378/4; 378/15;
378/20; 378/146; 378/99; 250/491.1;
250/492.3; 364/413.14; 364/413.15
[58] Field of Search ....................... 378/4, 20, 99, 205,
378/17, 11, 15, 145, 146, 147; 250/491.1, 492.3;
364/413.15, 413.14

[56] References Cited

U.S. PATENT DOCUMENTS

| | | | |
|---|---|---|---|
| 4,624,007 | 11/1986 | Muranushi | 378/4 |
| 4,630,202 | 12/1986 | Mori | 378/15 |
| 4,649,555 | 3/1987 | Matsubayashi | 378/4 |
| 4,789,929 | 12/1988 | Nishimura et al. | 378/20 |
| 5,046,003 | 9/1991 | Crawford | 378/15 |
| 5,060,246 | 10/1991 | Van Der Brug et al. | 378/20 |
| 5,073,911 | 12/1991 | Ozaki et al. | 378/17 |
| 5,090,037 | 2/1992 | Toth et al. | 378/4 |

FOREIGN PATENT DOCUMENTS 0041749 12/1981 European Pat. Off. .
0113879 7/1984 European Pat. Off. .
0117524 9/1984 European Pat. Off. .

Primary Examiner—David P. Porta
Assistant Examiner—Kim-Kwok Chu
Attorney, Agent, or Firm—Finnegan, Henderson, Farabow, Garrett and Dunner

[57] ABSTRACT

In an X-ray CT apparatus of a helical scanning scheme, a scannogram is obtained before acquiring projection data, and a range for which a tomographic image is desired, i.e., start and end positions of a helical scanning are designated on the scannogram. Helical scanning is started, not from a position of an object corresponding to the designated start position, but from a position preceding to the designated start position by a shift distance of the top plate corresponding to one cycle of helical scanning. Helical scanning is performed until a position over the designated end position by a shift distance of the top plate corresponding to one cycle of helical scanning. The projection data is acquired and is stored in correspondence with the scanning position. When reconstruction is to be performed, first, a desired slice position is designated on the scannogram. Projection data corresponding to a range preceding to the slice position by the shift distance of one cycle of helical scanning and a range succeeding to the slice position by the shift distance of one cycle are selected from the acquired data. Reconstruction is performed based on the selected projection data.

14 Claims, 4 Drawing Sheets

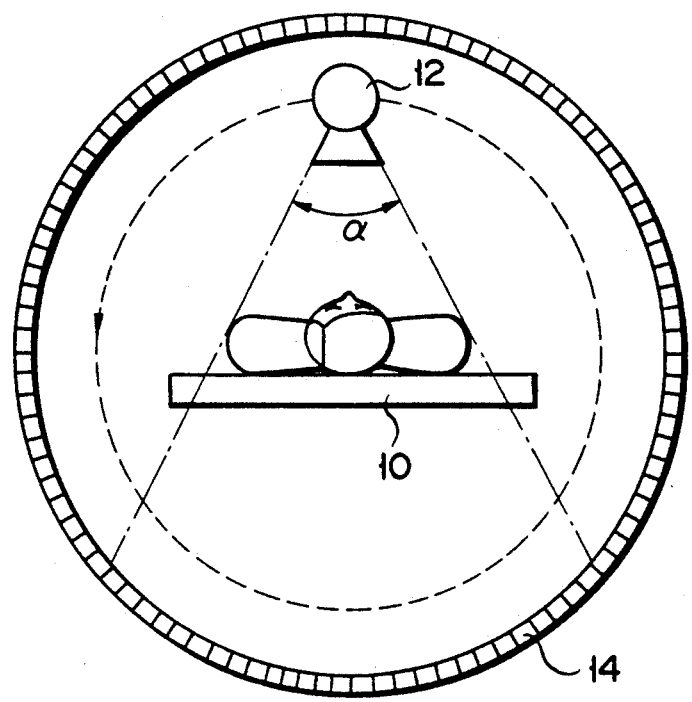
F I G. 2
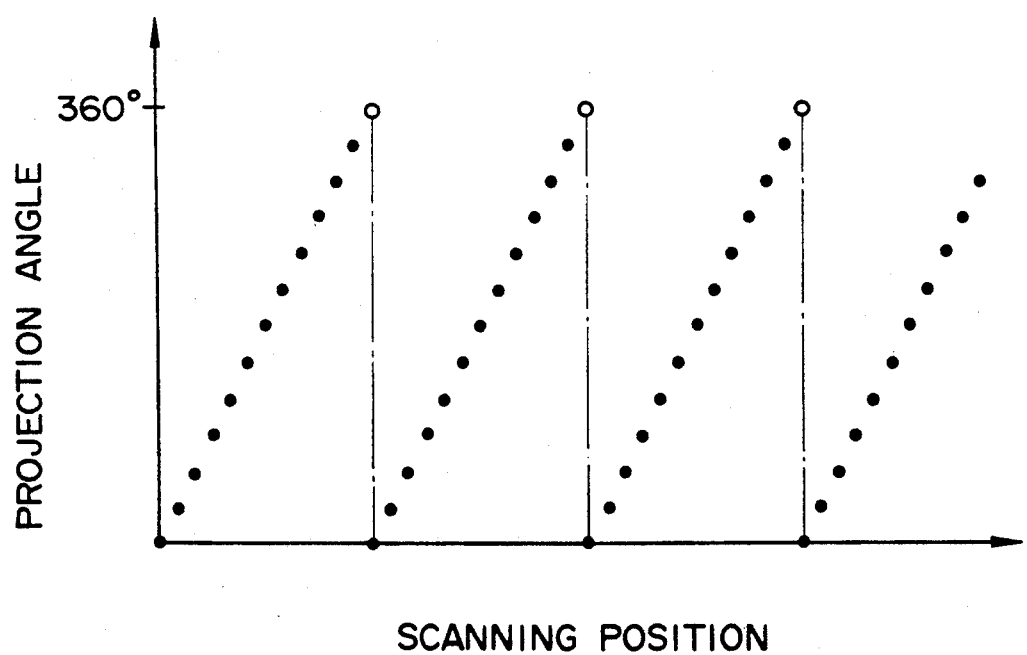
F I G. 3

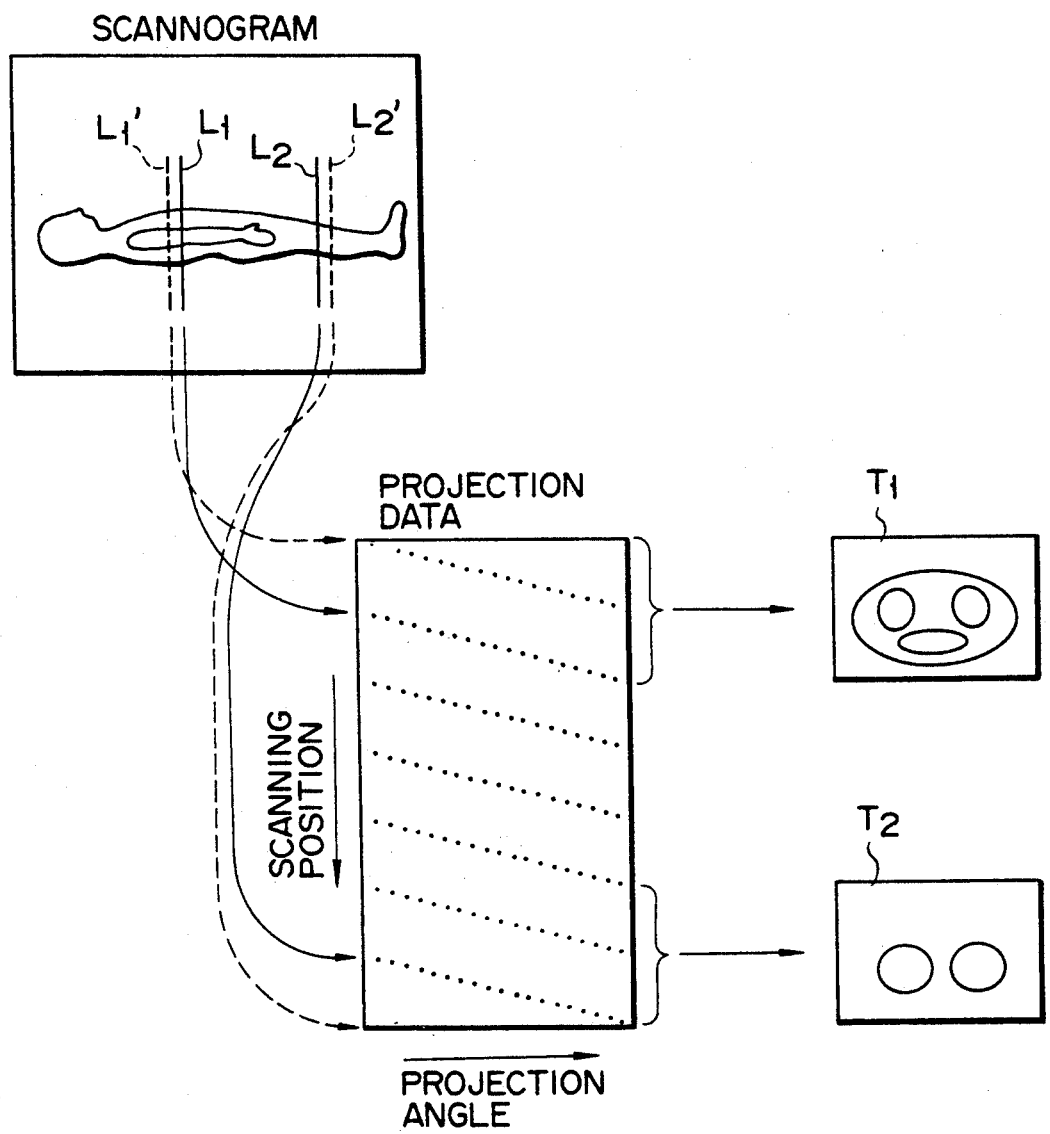
F I G. 4

COMPUTED TOMOGRAPHY SCANNER APPARATUS

BACKGROUND OF THE INVENTION

1. Field of the Invention

The present invention relates to a computed tomography scanner apparatus (to be simply referred to as a CT scanner hereinafter) and, more particularly, to a scan planning procedure or a reconstruction planning procedure of a CT scanner adopting a helical scanning scheme.

2. Description of the Related Art

Conventionally, when an object to be examined is scanned by an X-ray CT scanner, a so-called scan planning procedure or a reconstruction planning procedure is performed to suppress unnecessary X-ray radiation to the object and improve diagnostic efficiency by reconstructing only a tomographic image of a desired slice portion. In accordance with the scan planning procedure, it is determined before scanning which portion of the object is to be scanned to acquire projection data. In accordance with the reconstruction planning procedure, it is determined a tomographic image of which slice is to be reconstructed from the acquired projection data.

In the scan planning procedure, first, an X-ray tube is not rotated around the object but fixed immediately above or immediately beside the object. X-rays transmitted through the object are acquired while moving only the top plate of the bed in the direction of the body axis, and a scannogram of the object obtained by looking the object from the above or from its side is displayed. A scanning range is designated by using a line cursor on the scannogram. Then, the top plate is moved to cause the scanning position of the object to coincide with the start position of the designated scanning range. The top plate is then stopped and the X-ray tube is rotated around the object. Ordinary scanning is performed and projection data of the scanning position is acquired. After this, the top plate is moved at predetermined pitches. The top plate is stopped at every pitch shift and ordinary scanning is performed in the same manner. As a result, projection data acquired in units of scanning positions (top plate shift positions) are stored in an acquisition data memory.

When projection data of the entire scanning range are acquired, a slice to be reconstructed is designated again on the scannogram. Then, projection data at a scanning position corresponding to the designated slice is read out from the acquisition data memory, and a tomographic image of the designated slice is reconstructed based on the readout data.

An X-ray CT scanner of a helical scanning scheme has recently been developed in order to scan a large portion of an object at a high speed. In accordance with the helical scanning scheme, the top plate of the bed on which the object is placed is continuously moved in the direction of the body axis, and the X-ray tube is continuously rotated around the object, thereby scanning the object. In helical scanning, assuming that the object is stationary, the path of the relative movement of the X-ray tube seen from the side of the object becomes helical. In a CT scanner, in order to reconstruct a tomographic image of a certain slice, projection data of 360° (in the case of half scanning, 180°+fan angle) at a scanning position corresponding to the slice is required. In the case of helical scanning, however, since the top plate is also moved, only projection data of a single projection angle can be obtained at each scanning position. For this reason, projection data of other projection angles that cannot be obtained at a certain scanning position must be obtained by interpolation from two projection data obtained at the scanning positions on the two sides of the certain scanning position that have the same projection angle. The interpolation requires projection data for predetermined angles, for example, 360°. As a result, projection data for angles are necessary to reconstruct the tomographic image in the helical scanning scheme.

On the scannogram, however, the range corresponding to the projection data for angles necessary to reconstruct the tomographic image cannot be easily known. Therefore, a scanning range cannot be correctly designated on the scannogram with an X-ray CT scanner of the helical scanning scheme. For this reason, excessive X-rays may be radiated onto the object to be examined and unnecessary projection data may be acquired. Though the positional relationship between the scannogram data and the projection data is known, it is necessary to consider that auxiliary data for interpolation is required in addition to main data for reconstruction in order to reconstruct the tomographic image with an X-ray CT scanner of the helical scanning scheme. In the conventional reconstruction planning procedure, the tomographic image cannot be reconstructed at the end portion of the scannogram, since the auxiliary data is not considered.

SUMMARY OF THE INVENTION

Accordingly, it is an object of the present invention to provide a computed tomography scanner apparatus employing a helical scanning scheme to efficiently perform scanning by correctly designating a scanning range or a reconstruction position.

According to a first aspect of the present invention, there is provided a computed tomography scanner apparatus comprising means for obtaining a scannogram of an object by radiating a radiation ray onto the object, means for designating an arbitrary position on the scannogram, and means for obtaining projection data by helically scanning, with a radiation ray, a portion of the object including the designated position.

According to a second aspect of the present invention, there is provided a computed tomography scanner apparatus comprising means for helically scanning, with a radiation ray, an object to obtain projection data, means for obtaining a scannogram by radiating a radiation ray onto the object, means for designating an arbitrary position on the scannogram, and means for selecting projection data corresponding to a predetermined portion including the designated position from the obtained projection data to reconstruct a tomographic image of the designated position based on the selected projection data.

With the computed tomography scanner apparatus according to the first aspect of the present invention, a scannogram is obtained before helical scanning, an arbitrary position is designated on the scannogram, and only projection data required for reconstruction of the tomographic image of the designated position is acquired, thereby efficiently performing helical scanning.

With the computed tomography scanner apparatus according to the second aspect of the present invention, projection data corresponding to a predetermined portion including a position designated on the scannogram are selected from acquired projection data, and a tomographic image of the designated position is reconstructed based on the selected projection data, thereby reconstructing the tomographic image of the position designated on the scannogram.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 shows the positional relationship between an X-ray tube and an X-ray detector of the embodiment;

FIG. 3 shows projection data obtained by helical scanning;

FIG. 4 is a view for explaining a scan planning procedure for determining a scanning range from a scannogram.

DETAILED DESCRIPTION OF THE PREFERRED EMBODIMENTS

Figure 1:
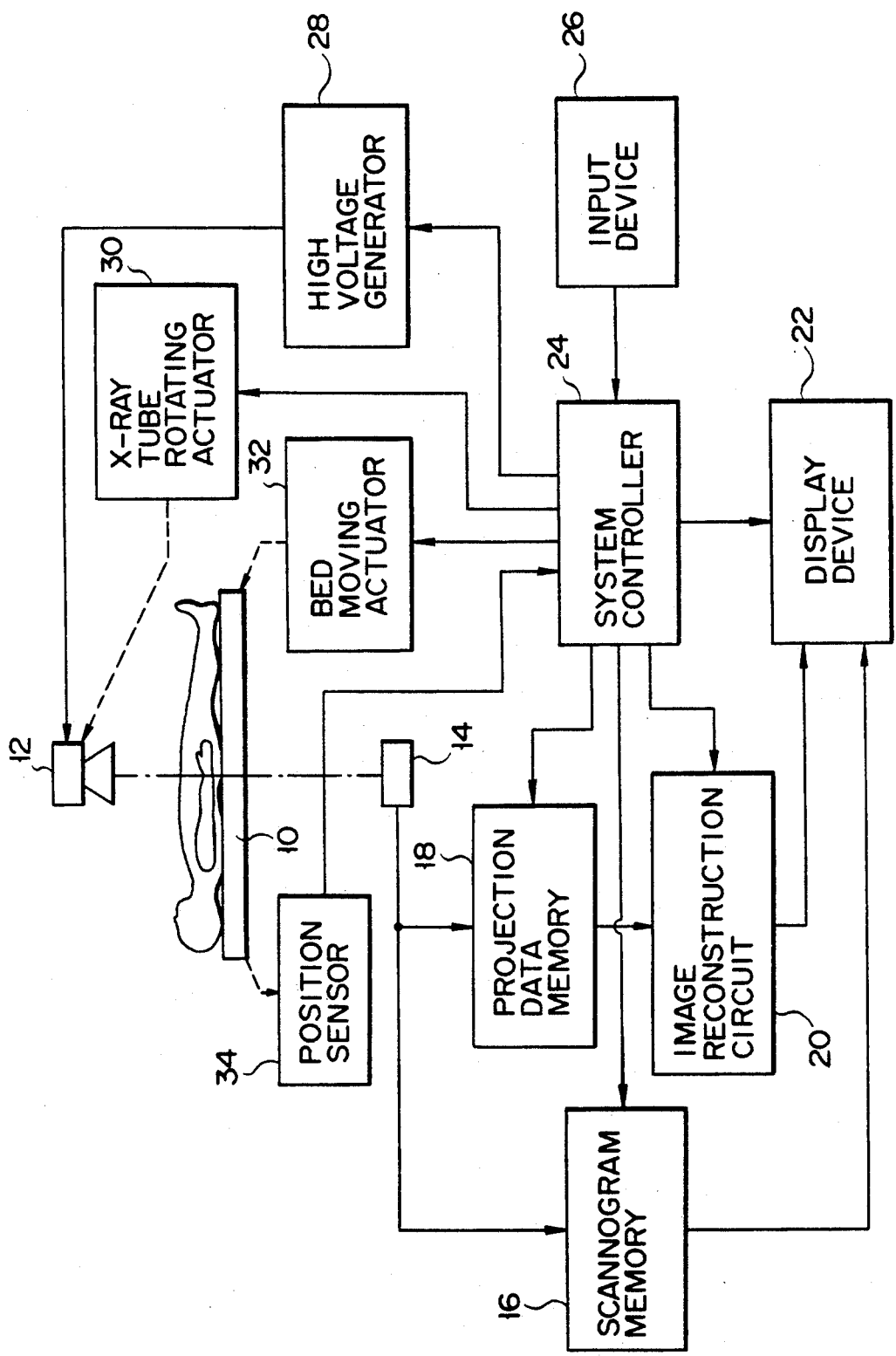
FIG. 1 is a block diagram of a computed tomography scanner apparatus according to an embodiment of the present invention.

A preferred embodiment of a computed tomography scanner apparatus according to the present invention will now be described with reference to the accompanying drawings. FIG. 1 is a block diagram showing the arrangement of the preferred embodiment. An object or patient to be examined is placed on a top plate 10 of a bed (not shown), and an X-ray tube 12 radiates X-rays onto the object in a fan-shaped manner in a plane crossing to the body axis of the object. The top plate 10 can move by projecting from the main body of the bed in the direction of the body axis of the object. An arbitrary slice of the object can therefore be located within the X-ray radiation/scanning plane. The X-ray tube 12 is held by a holding member (not shown) to be rotatable around the object, as shown in FIG. 2. A detector array 14 is arranged outside the rotation path of the X-ray tube 12 to entirely surround the object. Namely, this CT scanner is a fourth-generation apparatus. Note that the X-ray tube 12 can be provided outside the detector array 14. In this case, X-rays may be radiated in an oblique direction with respect to the detector array so that the X-rays radiated by the X-ray tube 12 may not be blocked by detectors before the object (between the X-ray tube and the object). Alternatively, the detector array must be arranged such that the detectors can move in the direction of the body axis, so that those before the object can temporarily escape from the X-ray radiation path upon X-ray radiation.

This embodiment has two operation modes. In the scannogram mode, the X-ray tube 12 is fixed immediately above or immediately beside the object, and the object is continuously moved in the direction of the body axis, so that the object is scanned with the X-rays in a planar manner. In the helical scanning mode, the X-ray tube 12 is continuously rotated around the object, and the object is continuously moved in the direction of the body axis, so that helical scanning with the X-rays is performed around the object. In the scannogram mode, the outputs from all the detectors of the detector array 14 are not used, but only the outputs from the detectors irradiated by the fan-shaped X-rays are used. A scannogram memory 16 has memory locations corresponding to the X-ray radiation planes of the object. Signals output from the irradiated detectors are written at memory locations of the scannogram memory 16 corresponding to the X-ray radiation positions (respective detectors), thus forming a scannogram. In the helical scanning mode, projection data of a certain projection angle is obtained in units of scanning positions (top plate positions) of the object, as shown in FIG. 3. The projection data output from the detector array 14 during the helical scanning mode is written in a projection data memory 18. Although not shown in the drawings, a preprocessor for obtaining projection data by amplifying, integrating, or D/A converting an output signal from the detector array 14 is connected to the input stage of the projection data memory 18. Each projection data is stored in the memory 18 in correspondence with a scanning position and a projection angle under control of a system controller 24 to be described later.

An output from the projection data memory 18 is supplied to an image reconstruction circuit 20, and a tomographic image is reconstructed from projection data for predetermined angles concerning a certain slice. The predetermined angles differ depending on the reconstruction schemes. It may be 360° for a full scan mode or 180° +fan angle c for a half scan mode.

In the helical scanning scheme, only projection data of a single projection angle is present for each scanning position. Therefore, projection data of the remaining projection angles must be obtained by interpolation of two projection data sandwiching the current scanning position and having the same projection angle. With an interpolation method for using 360° data, in order to interpolate projection data of 360° or 180°+fan angle $\alpha 0$ of a certain slice, projection data for a scanning range corresponding to 760° (two helical cycles) or 540°+$\alpha$ with the slice as the center are needed. For this purpose, when a certain slice is designated, projection data for predetermined projection angles with the slice as the center are supplied from the memory 18 to the image reconstruction circuit 20. A scannogram output from the scannogram memory 16 and a tomographic image output from the image reconstruction circuit 20 are supplied to a display device 22 and displayed on it.

The system controller 24 is provided for the overall control. An input device 26 for setting various conditions is connected to the system controller 24. The system controller 24 is also connected to the scannogram memory 16, the projection data memory 18, the image reconstruction circuit 20, and the display device 22. The system controller 24 controls a high voltage generator 28 for supplying a drive signal to the X-ray tube 12 and the X-ray tube holding member. As a result, control signals are supplied to an X-ray tube rotating actuator 30 for rotating the X-ray tube 12, and to a bed moving actuator 32 for moving the top plate 10. The position of the top plate 10 is detected by a position sensor 34 and input to the system controller 24.

The operation of this embodiment will be described. First, the scan planning procedure will be described with reference to FIG. 4. In the scan planning procedure, the scannogram mode is first executed, and it is determined, on a scannogram, a portion for which a tomographic image is to be obtained, i.e., which range, is to be scanned. As described above, the X-ray tube 12 is fixed immediately beside the object to be examined, only the top plate 10 is continuously moved at a constant speed, and the scannogram of the entire sample body is scanned and displayed on the display device 22. Line cursors $L_1$ and $L_2$ are displayed on the scannogram by the operation of the input device 26, and a range between the cursors is designated as the scanning range. A shift distance of the top plate 10 during one cycle of the helical scanning is known from the moving speed of the top plate 10 and the rotating speed of the X-ray tube 12. Therefore, the system controller 24 can determine the acquisition range of projection data required for reconstructing tomographic images of the start and end positions of the scanning range. More specifically, in an interpolation method using 360° projection data, a position $L_1'$ outside the position designated by the line cursor $L_1$ by a distance corresponding to a shift distance of the top plate 10 during one cycle of the helical scanning is determined as the projection data acquisition start position, and a position $L_2'$ outside the position designated by the line cursor $L_2$ by a distance corresponding to a shift distance of the top plate 10 during one cycle of the helical scanning determined as the projection data acquisition end position. Hence, an acquisition range $L_1'$ to $L_2'$ of the projection data required for reconstruction of the range sandwiched between the line cursors $L_1$ and $L_2$ is determined. The system controller 24 controls the bed moving actuator 32 and the X-ray tube rotating actuator 30 to acquire the projection data of this range $L_1'$ to $L_2'$ and performs helical scanning. The projection data obtained by the detector array 14 is stored in the memory 18 together with the rotating angle (projection angle) of the X-ray tube 12 in units of top plate positions (scanning positions) detected by the position sensor 34. FIG. 4 shows tomographic images $T_1$ and $T_2$ of the slices designated by the cursors $L_1$ and $L_2$. In this manner, only the projection data necessary for reconstruction tomographic images within the desired range of the object can be efficiently acquired in correspondence with the scanning position. Projection data of an unnecessary portion is prevented from being acquired, and the data acquisition time can be shortened. Also, unnecessary X-ray radiation onto the object is prevented.

Figure 5:
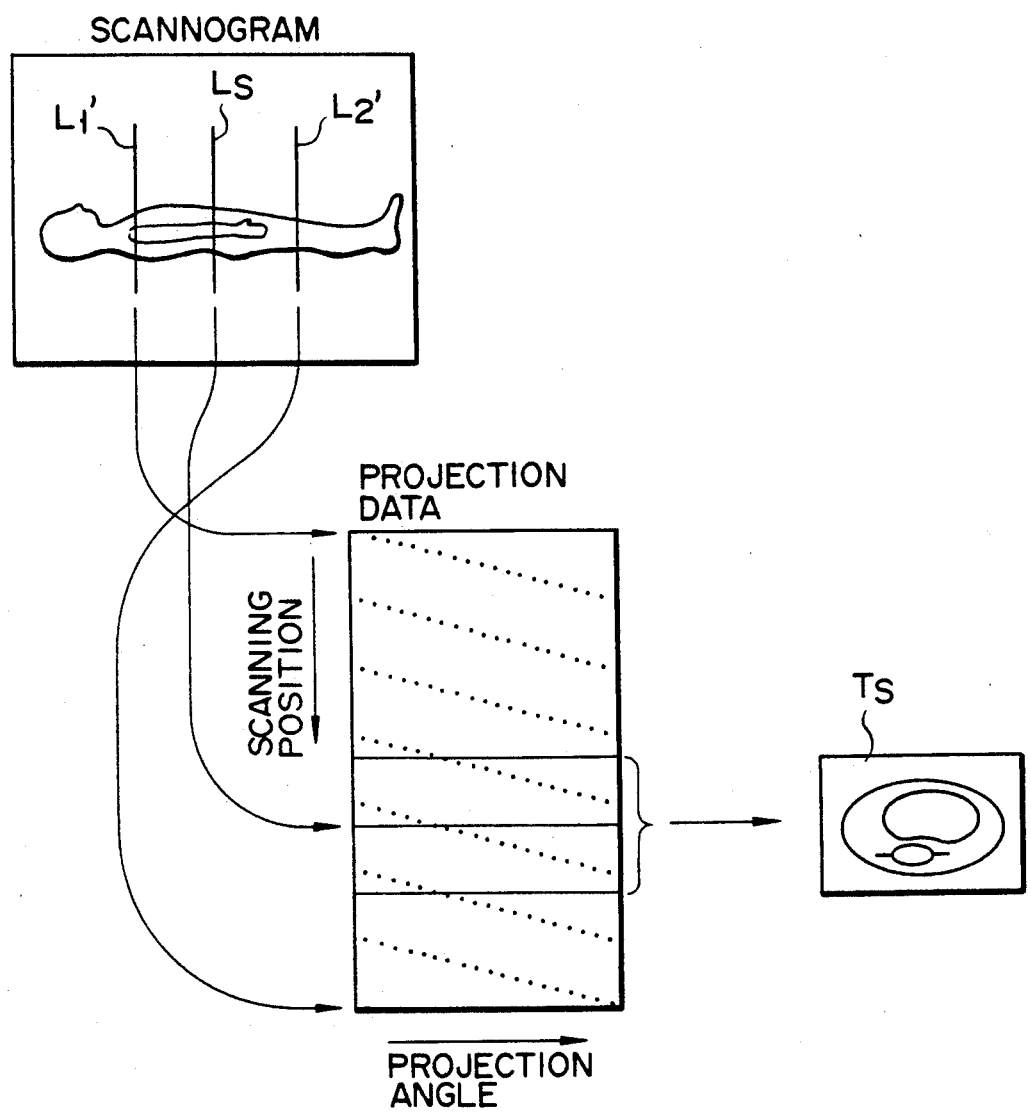
FIG. 5 is a view for explaining a reconstruction planning procedure for reconstructing a tomographic image of a position designated on the scannogram from acquired projection data.

In general, tomographic images in units of scanning positions of a predetermined pitch are sequentially reconstructed from the projection data acquired in this manner and displayed. If a desired tomographic image is found among these tomographic images, no further operation is needed. However, if the operator wishes to obtain a tomographic image of an arbitrary scanning position in a single pitch, its slice position must be designated on the scannogram by using the line cursor. This operation, called a reconstruction planning procedure, will be described with reference to FIG. 5. First, assume that linear cursors $L_1'$ and $L_2'$ indicating the range of the acquired projection data are displayed on the scannogram by the operation of FIG. 4. When an arbitrary slice in this range is designated by a linear cursor $L_s$, projection data for two cycles of helical scanning with the line cursor $L_s$ as the center, which corresponds to a projection angle of 720°, if the full scan mode and the interpolation method using 360° projection data are employed, are read out from the memory 18 and supplied to the image reconstruction circuit 20. As a result, a tomographic image $T_s$ of the slice designated by the line cursor $L_s$ on the scannogram is reconstructed and displayed.

As has been described above, according to the present invention, a scannogram is obtained prior to tomographic scanning, and an arbitrary range is designated on the scannogram. Only projection data required for reconstruction of the tomographic images of the designated range can be acquired, resulting in efficient tomographic scanning. In place of designating a range, a scanning position may be directly designated on the scannogram, and only the scanning position range corresponding to two cycles of helical scanning preceding an succeeding to the designated scanning position may be helically scanned. According to the present invention, projection data corresponding to two cycles of helical scanning with the position designated on the scannogram as the center can be selected from the acquired projection data, and a tomographic image of the designated position can be reconstructed based on the selected projection data, thereby reconstructing the tomographic image of the position designated on the scannogram.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the interpolation method is not limited to the above method using 360° projection data, but it is possible to interpolate the projection data of one slice position using the counterbeam. In this interpolation method, it is not necessary to use 360° projection data but the projection data of less than 360° can interpolate the projection data of one slice position. The radiation rays for scanning the object are not limited to X-rays, and another type of radiation rays such as gamma rays may be used instead. The embodiment has been described with reference to a fourth-generation CT scanner. However, the present invention can also be applied to third and fifth-generation CT scanners. In the embodiment, a scannogram is scanned first to determine the scanning range. However, if it is not necessary to determine a scanning range, helical scanning may be performed at once to acquire projection data. Then, a scannogram may be scanned, a slice to be reconstructed may be designated, and only the designated slice may be reconstructed.

What is claimed is:

1. A computed tomography scanner apparatus comprising:

first means for obtaining tomographic image data of an object by helically scanning the object with a radiation ray;

second means for obtaining one-directional projection image data of the object by radiating a radiation ray onto the object;

means for designating a desired slice on the one-directional projection image data obtained by said second means; and third means for selecting, from tomographic image data obtained by said first means, data corresponding to a predetermined range including the desired slice designated by said designating means and obtaining a tomographic image of the designated slice from the data thus selected.

2. An apparatus according to claim 1, wherein said third means selects first tomographic image data for projection angles required for reconstructing the tomographic image and second tomographic image data for interpolating the tomographic image data for the projection angles required for reconstructing the tomographic image.

3. An apparatus according to claim 1, wherein said third means selects tomographic image data corresponding to two cycles of helical scanning with the designated slice position as the center.

4. A computed tomography scanner apparatus comprising:

first means for obtaining tomographic image data of an object by helically scanning the object with a radiation ray;

second means for obtaining one-directional projection image data of the object by radiating a radiation ray onto the object;

means for designating a desired range on the projection image data obtained by said second means; and third means for limiting a portion of the object helically scanned by said first means so as to obtain tomographic image data corresponding to a range as a sum of the desired range designated by said designating means, a first predetermined range preceding to the desired range, and a second predetermined range succeeding to the desired range.

5. An apparatus according to claim 4, wherein each of said first and second predetermined ranges corresponds to one cycle of helical scanning.

6. A computed tomography scanner apparatus comprising:

means for obtaining a scannogram of an object by radiating a radiation ray onto the object;

means for designating an arbitrary position on the scannogram; and helical scanning means for obtaining a tomographic image by helically scanning, with a radiation ray, a portion of the object corresponding to a predetermined range including the position designated by said designating means.

7. An apparatus according to claim 6, wherein said helical scanning means scans a range corresponding to two cycles of helical scanning with the designated position as the center.

8. An apparatus according to claim 7, wherein said helical scanning means obtains, by interpolation, projection data for predetermined projection angles of the designated position from projection data of the same projection angle preceding and succeeding to the designated position, and thereafter reconstructs the tomographic image of the designated position.

9. A computed tomography scanner apparatus comprising:

means for obtaining a scannogram of an object by radiating a radiation ray onto an object;

first designating means for designating an arbitrary range on the scannogram;

helical scanning means for obtaining projection data by helically scanning a portion of the object, with a radiation ray, the portion corresponding to a range as a sum of the range designated by said designating means, a first predetermined range preceding to the desired range, and a second predetermined range succeeding to the desired range;

means for storing projection data obtained by said helical scanning means;

second designating means for designating an arbitrary position on the scannogram; and means for obtaining a tomographic image by reading out, from said storing means, projection data corresponding to a third predetermined range preceding to the position designated by said second designating means and a fourth predetermined range succeeding to the position designated by said second designating means.

10. An apparatus according to claim 9, wherein said first, second, third, and fourth predetermined ranges each corresponds to one cycle of helical scanning.

11. A computed tomography scanner apparatus comprising:

helical scanning means for obtaining projection data by helically scanning an object with a radiation ray, and storing the projection data in correspondence with the position of the object along a scanning direction;

means for obtaining a scannogram by radiating a radiation ray onto the object;

means for designating an arbitrary position on the scannogram; and means for reading out, from said helical scanning means, projection data corresponding to a predetermined portion including the position designated by said designating means and reconstructing a tomographic image of the position designated by said designating means.

12. An apparatus according to claim 11, wherein said reconstructing means reads out projection data of a range corresponding to two cycles of helical scanning with the designated position a the center from said helical scanning means.

13. An apparatus according to claim 12, wherein said reconstructing means reconstructs the tomographic image after interpolating projection data of the projection angle of the designated position from projection data preceding and succeeding to the designated position of the same projection angle.

14. An apparatus according to claim 13, wherein said designating means designates a reconstruction range by designating two positions, and said reconstructing means performs reconstruction at predetermined intervals within the designated range

* * * * *

UNITED STATES PATENT AND TRADEMARK OFFICE
CERTIFICATE OF CORRECTION

PATENT NO. : 5,212,717
DATED : May 18, 1993
INVENTOR(S) : Tetsurou Hada

It is certified that error appears in the above-indentified patent and that said Letters Patent is hereby corrected as shown below:

Claim 12, column 8, line 50, change "a" to --as--.

Claim 14, column 8, penultimate line after "range" insert --.--.

Signed and Sealed this

Seventeenth Day of May, 1994

Attest:

BRUCE LEHMAN

Attesting Officer    Commissioner of Patents and Trademarks